(12) United States Patent
Sarrafzadeh et al.

(10) Patent No.: US 9,891,701 B2
(45) Date of Patent: *Feb. 13, 2018

(54) APPARATUS, SYSTEM, AND METHOD FOR AUTOMATIC IDENTIFICATION OF SENSOR PLACEMENT

(75) Inventors: Majid Sarrafzadeh, Anaheim Hills, CA (US); Ani Nahapetian, Glendale, CA (US); Alireza Vahdatpour, Kirkland, WA (US); Mahsan Rofouei, San Jose, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 852 days.

This patent is subject to a terminal disclaimer.

(21) Appl. No.: 14/002,665

(22) PCT Filed: Mar. 2, 2012

(86) PCT No.: PCT/US2012/027608
§ 371 (c)(1),
(2), (4) Date: Oct. 17, 2013

(87) PCT Pub. No.: WO2012/119126
PCT Pub. Date: Sep. 7, 2012

(65) Prior Publication Data
US 2014/0032165 A1 Jan. 30, 2014

Related U.S. Application Data

(60) Provisional application No. 61/448,609, filed on Mar. 2, 2011.

(51) Int. Cl.
G06F 3/01 (2006.01)
G01C 22/00 (2006.01)
A61B 5/11 (2006.01)

(52) U.S. Cl.
CPC .......... G06F 3/011 (2013.01); A61B 5/1112 (2013.01); G01C 22/006 (2013.01)

(58) Field of Classification Search
None
See application file for complete search history.

(56) References Cited

U.S. PATENT DOCUMENTS 6,571,193 B1 * 5/2003 Unuma ............... A43B 3/0005
340/853.2
2004/0077958 A1 4/2004 Hiroyuki et al.
(Continued)

FOREIGN PATENT DOCUMENTS

KR 20-0361681 9/2004

OTHER PUBLICATIONS

International Search Report PCT/US2012/027608 dated Sep. 21, 2012.

*Primary Examiner* — An Do
*Assistant Examiner* — Renee I Wilson
(74) *Attorney, Agent, or Firm* — Foley & Lardner LLP; Cliff Z. Liu (57) ABSTRACT

A location of a sensor is determined by: (1) receiving time series data including components in a plurality of dimensions, wherein the time series data correspond to measurements of the sensor that is applied to a subject; (2) determining a plurality of subsequences associated with the time series data, wherein each of the plurality of subsequences represents a characteristic pattern projected along one of the plurality of dimensions; (3) identifying a correlated subset of the plurality of subsequences as at least one instance of an activity of the subject; and (4) based on features of the correlated subset, determining the location of the sensor as applied to the subject.

17 Claims, 4 Drawing Sheets

(56) References Cited

U.S. PATENT DOCUMENTS

2006/0161079 A1     7/2006   Ji-Hyun et al.
2008/0281234 A1   11/2008   Goris et al.
2012/0109872 A1*   5/2012   Havinga ................ H04L 67/12
                                                                                                                      706/52

* cited by examiner

APPARATUS, SYSTEM, AND METHOD FOR AUTOMATIC IDENTIFICATION OF SENSOR PLACEMENT

CROSS-REFERENCE TO RELATED APPLICATION

This application is a National Stage Entry of PCT/US2012/027608 filed on Mar. 2, 2012, which claims the benefit of U.S. Provisional Application Ser. No. 61/448,609 filed on Mar. 2, 2011, the disclosure of which is incorporated herein by reference in its entirety.

FIELD OF THE INVENTION

The invention generally relates to sensor placement and, more particularly, to the automatic identification of sensor placement.

BACKGROUND

Recent advances in embedded systems technology have resulted in utilization of wearable and non-intrusive devices for remote health and activity monitoring. Pedometers and smart phones with motion sensors are among devices that are used to continuously monitor characteristics such as daily activity and exercise. With the production of ultra low power sensor interfaces, smart band aids can be used for health and medical monitoring applications. For example, smart band aids can be used for monitoring metrics such as daily energy expenditure, body temperature, skin moisture, heart rate, and other human vital signs. The proliferation of these wearable devices results in a higher diversity of applications of these devices. In order to be non-intrusive in daily activities, these devices should be adaptable to habits of individual users. For example, individual users may place these devices on different regions of their bodies, which can affect how the data measured by these devices should be interpreted.

It is against this background that a need arose to develop the apparatus, system, and method described herein.

SUMMARY

One aspect of the invention relates to a non-transitory computer-readable storage medium. In one embodiment, the storage medium includes executable instructions to: (1) receive time series data including components in a plurality of dimensions, wherein the time series data correspond to measurements of a sensor that is applied to a subject; (2) determine a plurality of subsequences associated with the time series data, wherein each of the plurality of subsequences represents a characteristic pattern projected along one of the plurality of dimensions; (3) identify a correlated subset of the plurality of subsequences as at least one instance of an activity of the subject; and (4) based on features of the correlated subset, determine a location of the sensor as applied to the subject.

Another aspect of the invention relates to a system for sensor localization. In one embodiment, the system includes: (1) a processing unit; and (2) a memory connected to the processing unit and including executable instructions to: (a) identify a portion of a multi-dimensional time series as at least one instance of physical movement of a subject, wherein the multi-dimensional time series correspond to measurements of a sensor that is applied to the subject; (b) selectively process the portion of the multi-dimensional time series to derive a set of features associated with the physical movement; and (c) based on the set features, determine a location of the sensor as applied to the subject.

Other aspects and embodiments of the invention are also contemplated. The foregoing summary and the following detailed description are not meant to restrict the invention to any particular embodiment but are merely meant to describe some embodiments of the invention.

BRIEF DESCRIPTION OF THE DRAWINGS

For a better understanding of the nature and objects of some embodiments of the invention, reference should be made to the following detailed description taken in conjunction with the accompanying drawings.

DETAILED DESCRIPTION

1. Introduction

In some embodiments, there are at least four reasons why it is beneficial to automatically discover the location or placement of wearable monitoring devices on a user's body.

1) Correctness: Wearable, non-intrusive embedded devices can be used to remotely and continuously monitor conditions of subjects such as basal body temperature, skin moisture, heart rate, and ultraviolet exposure. Correct interpretation of data from these monitoring devices can depend on correct placement of these devices on a subject's body. For example, the following table summarizes normal temperature range variation for normal adults according to placement of a thermometer on the body:

TABLE 1

Normal Temperature Readings for Different Regions on the Body

| Location | Ear | Axilla | Rectal | Oral |
|---|---|---|---|---|
| Range (° C.) | 35.5-38 | 35.5-37 | 34.5-38 | 33-38 |

As shown in Table 1, temperature can vary in different body parts. If at different times a user attaches his temperature monitoring device to different regions on his body, clinicians and caregivers can be misguided by the data variation. Therefore, it is desirable for clinicians to know the placement of the sensing device on the body, so that the data collected from the device becomes valuable, and its analysis results in correct interpretation.

2) Accuracy: The operation of motion and energy expenditure monitoring systems can depend on the placement and orientation of motion sensors, which typically include accelerometers and gyroscopes. As shown in Table 2, the operation of pedometers is an example of the effect of device placement on the accuracy of data measured by the device. The step counting accuracy can change if the pedometer is attached to the body anywhere other than the waist, because the user's movements can be projected differently on an accelerometer included in the pedometer. In an experiment, 6 pedometers were attached to different regions on a subject's body, and the subject was asked to take 220 steps. The following table shows how the locations of the pedometers impact the number of steps counted by each pedometer:

TABLE 2

Counted Steps Versus Pedometer Location

| Pedometer location | waist | shin | thigh | forearm | upper arm | chest |
|---|---|---|---|---|---|---|
| Steps counted | 230 | 238 | 148 | 181 | 177 | 0 |
| Error $\left(\frac{real - est.}{real}\right)$ | 4% | 8% | 32% | 17% | 19% | 100% |

In a location-aware pedometer, a dynamic threshold control technique can enhance the accuracy of the step counting. Energy expenditure estimation via motion sensing is another application where accuracy can depend on the accurate classification of the type of the movement performed by the user (e.g., walking, jogging, running, jumping, and so forth) and the placement of the accelerometer on the body. If a user wears an accelerometer on her foot instead of her waist, the accuracy of the activity detection can degrade. This is because the activity detection models implemented in the device can be tuned for waist motions. As a result of inaccurate activity detection, the result can be an overestimation or underestimation of the user's caloric expenditure.

3) Communication Optimization: The human body can affect the performance of radio transceivers. The wireless communication loss rate can depend on the location of a sensor, since, for example, the body can reduce the transmission range of a device. Automatic on-body localization can allow sensing devices to control communication power according to anticipated channel quality or loss rate.

4) Usability and Adaptability: It is desirable for monitoring systems to allow users to change the placement of wearable sensors according to their life styles, clothing, and activities. Not only does on-body device localization enhance the usability of these devices, but it also allows the design of smarter devices, which can automatically adapt to users and their environment, such as by automatically controlling device operation or automatically selecting operation modes. Different placement of a device on the body can be interpreted as a request by a user for a particular application or a change in the environment. For example, automatic device localization can allow smart phones to rapidly and autonomously adapt to user needs. In one case, as soon as a user mounts a smart phone on her upper arm, the smart phone can activate its gym/music mode.

2. Overview

Described herein is a technique for automatic on-body device localization. In one embodiment, the on-body device localization is performed based on acceleration data. An accelerometer is one commonly used type of motion sensor. For example, an accelerometer can be used for a variety of applications such as device orientation detection, game controlling, shock protection, and activity discovery. Given that accelerometers are relatively inexpensive and consume low energy, these devices can be embedded in many high-end and portable systems. The developed technique can utilize acceleration data associated with any monitoring device to determine the location where it has been applied on the body, and allows both on-line and off-line discovery of device location on the body. Acceleration data can be analyzed to discover the placement of the sensor on the body, since different parts of the body, such as different organs, can exhibit different activity characteristics. This capability and technology can be added to sensors and other monitoring devices that are placed on a body (human or animal), without requiring any data input regarding the placement location of the sensor and monitoring device.

In some embodiments, the technique includes two main phases: unsupervised activity discovery and supervised location estimation. The technique for location estimation includes two main sub-phases: hosting body part discovery and estimation of sensor location and orientation.

A noteworthy aspect of on-body localization is to analyze data, such as acceleration data, measured when a user is performing a specific activity. For example, walking is typically a frequent and consistent activity that people perform throughout the day. Hence, the walking activity can be used as a characterizing activity for the device localization technique. However, since the placement and orientation of sensors on the body is not known a priori (and may change in each use), projection of body movement patterns on the sensors may not be predictable.

Supervised techniques for activity detection using on-body sensors have been studied in recent years. These techniques can leverage body-fixed sensors and predefined models for activities. In contrast, an improved approach for unsupervised classification of human activities is designed to determine activity models during run-time, without predefining activity models and patterns in a setup phase. As a result, this approach is not only applicable in accessories and wearable systems (with higher diversity in discovering the location), but also can be leveraged in smart band aids and electronic implants. The unsupervised activity detection technique is described further below. Certain aspects of the unsupervised activity detection technique are also described in U.S. Provisional Application Ser. No. 61/448,602, "Apparatus, System, and Method for Discovering Abnormalities in Behavior and Activities in Multi-Dimensional Data," Sarrafzadeh et al., filed Mar. 2, 2011, which is herein incorporated by reference in its entirety.

In one embodiment, an unsupervised technique discovers walking activity occurrences based on their frequency and consistency during long time intervals. Once time series subsequences representing walking activity are discovered, these subsequences are analyzed with a supervised classification technique. In one embodiment, a support vector machine (SVM) estimates the location of the device based on at least one of the frequency and the time domain features of the time series subsequences that represent the walking activity. For example, the location of the device can correspond to one or more hosting organs (or other body parts).

In order to discover the hosting body part, variation of data measured by sensors, such as acceleration data, is analyzed. For example, arm motion can have a higher degree of freedom than various other regions of the body, while a greater difference is observed between minimum and maximum values of acceleration, such as acceleration in each of three spatial dimensions, in leg motion data than in data measured by sensors placed on various other regions of the body.

Figure 1:
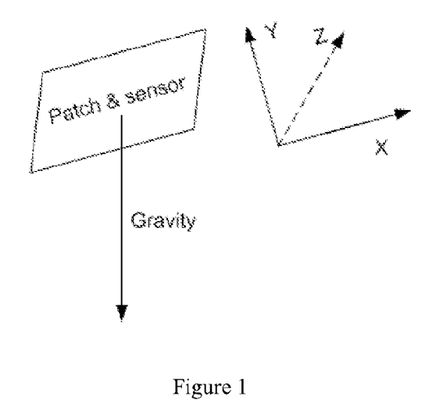
FIG. 1: The earth's gravity and an oriented sensor, according to an embodiment of the invention.

Upon estimation of the location of the sensor on the body (hosting body part, such as arm, leg, foot, waist, and so forth), stationary data for accelerometers can be used to derive the orientation of the sensor on the body, such as the relative positioning of the sensor relative to the hosting body part to which the sensor is applied. This phase can be carried out using the projection of the earth's gravity on the accelerometer. In the absence of motion, accelerometer data can be used to discover the exact orientation of a sensor with respect to the ground. Therefore, the process should first locate a semi-stable time interval in the sensor data, and then evaluate the orientation of the sensor based on the 3-dimensional acceleration data (FIG. 1). For example, knowing that the sensor is placed on the arm, the orientation data can specify whether the sensor is located beneath, on top, or on the side of the arm.

Other information, such as information regarding bony prominence, can be used to break symmetry in certain regions on the body. In certain cases and for certain activities, symmetry can be broken using the notion that humans can be predisposed to single hand dominance.

The information from the sensor location identification can be used to calibrate measurements. For example, temperature measurement can vary widely across the body. Humidity and pressure readings can also be affected by sensor location. The identification can determine where the sensor has been placed, across regions of distinction. The body can be partitioned into regions of distinction, across which variations in the location of the sensor can be determined. In one embodiment, the regions of distinction correspond to hosting body parts or to portions of the hosting body parts, such as upper arm, forearm, and so forth.

In one embodiment, the on-body localization technique can be incorporated into a wound management system that analyzes the data obtained from a continuous monitoring device. The automatic identification of sensor placement can allow a plug-and-play use of various sensors, including a smart band aid. The on-body localization technique can eliminate the need to place a monitoring device in a specific or pre-determined body part. Additionally, the technique can eliminate the need to identify and associate a specific region on the body with sensor device placement.

3. Activity Discovery

Motif detection in time series data is one technique to discover recurrent subsequences in a longer time series. However, motif discovery can be computationally intensive and may be less desirable for embedded computing and applications with a large amount of data. Hence, a different technique is used for discovering a recurrent activity in time series data. In one embodiment, this activity is walking, and the data is three-dimensional accelerometer data. Alternatively, the activity may involve other types of physical movement, such as running, jumping, lifting, writing, and so forth. The activity can be a frequent activity represented by the data, such as the most frequent activity represented by the data.

In one embodiment, the technique for activity discovery includes two stages. In the first stage, each dimension of sensor data, such as accelerometer data, is processed separately (serially or in parallel) to detect or discover recurrent patterns. In one embodiment, a binning approach is used to classify similar patterns in single-dimensional accelerometer data. In the second stage, classified patterns are grouped together with a clustering approach to detect activities. Below, each stage of the activity discovery technique is described.

3.1 Problem Formulation

This section sets forth certain specifications and notations used in remaining sections for some embodiments of the invention. Note that certain terms will be understood to one of ordinary skill in the art, such as time series, subsequence, Euclidean distance, and so forth, and those terms need not be further elaborated below.

SPECIFICATION 3.1. Multi-dimensional time series: a multi-dimensional time series $M=\{T_1, \ldots, T_q\}$ includes q time series with equal length (n). The specification of equal length can be modified or relaxed for some embodiments.

SPECIFICATION 3.2. Multi-dimensional subsequence: a multi-dimensional subsequence $S=\{s_1, \ldots, s_p\}$ includes p subsequences, where there exists at least one subsequence $s_i$, $1 \leq i \leq p$ such that $s_i$ has temporal overlap with at least another (or all other) subsequences in S.

Note that the members of S can be scattered among any subset of dimensions of a multi-dimensional time series M (e.g., $p \leq q$). In addition, the members of S can be different in the shape and length.

SPECIFICATION 3.3. Activity: an activity is a multi-dimensional subsequence $A=\{a_1, \ldots, a_x\}$ with recurrent occurrences in the multi-dimensional time series. The occurrences of the activity A are noted as $A^1 \ldots A^k$, when A has k occurrences.

3.2 Activity Primitive Discovery in Single-Dimensional Time Series

Figure 2:
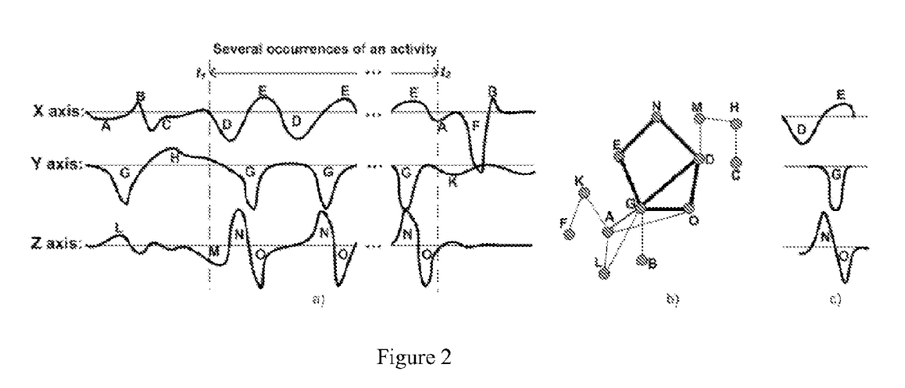
FIG. 2: An example of a clustering technique for recurrent activity discovery, according to an embodiment of the invention: (a) three dimensions of accelerometer data, with several occurrences of an activity between $t_1$ and $t_2$; (b) The interval coincidence graph, representing primitives in the time series data. The thickness of edges show higher coincidence between the primitives; and (c) Primitives with high coincidence are clustered, and the recurrent activity is discovered. $t_1$ and $t_2$ are sent to output as the start and end time of the activity.

Patterns in single-dimensional accelerometer data can be classified based on the movement that results from an activity along a corresponding axis. In one embodiment, the corresponding axis is along one of three spatial dimensions. An activity primitive can be specified as a subsequence between two consecutive stable regions (or default sensor values) in the time series. In one embodiment, a stable region of a signal corresponds to a time interval during which the value of the signal remains between (average (or mean) value of the signal−X) and (average (or mean) value of the signal+X), where X can be between from about 0.1 and about 1.0 times a standard deviation of the signal. For example, X can be a value between from about 0.3 to about 0.7 times or from about 0.4 to about 0.6 times the standard deviation of the signal, such as 0.5 times the standard deviation of the signal. Such subsequences are sometimes observed as bell shape patterns (with local minimum or maximum points) or linear slopes between two stable values, which, depending on the speed and nature of the activity, can have different length and frequency. The acceleration data can be converted to displacement, using the following equation on a subsequence $(a_1\ a_2\ \ldots\ a_m)$ of length m.

$$\text{displacement} = D \cdot \sum_{k=1}^{m} \sum_{i=1}^{k} |a_i - a_1|$$

where D is the calibration constant factor, which depends on the placement of the sensor and other parameters such as the frequency of data sampling. Although the location of the sensor in not known a prior, since the displacement information is used to compare patterns for the same sensor, it is effectively constant for all patterns and can be eliminated from the calculations. FIG. 2(a) depicts three accelerometers and several activity primitives classified for them (labeled by letters of the alphabet).

Methodology 1, shown in Table 3, presents a technique for extracting activity primitives as subsequences projected on single-dimensional time series. The technique extracts patterns from the time series, classifies the patterns based on the physical attribute of the data and according to a discretization cardinality, and assigns a symbol to each pattern. It also assigns a starting time to each symbol. Here, in order to discretize the calculated displacement and assign symbols, the technique considers a probability distribution of the calculated displacements and assigns symbols to primitives such that primitives are classified considering the variation of displacement during application execution.

TABLE 3

Methodology 1: Single-dimensional activity primitive extraction

```
Input: Time series T = t_1..t_n
Output: List of activity primitives along with their occurrences
    location p_occurrence(1..j), start(1..j)
i ← 1
while true do
    while t_i = default_value | t_i is stable region
    do
        increment i
    end while
    start(j) ← i
    while t_i ≠ default_value & t_i is not stable region
    do
        d ← d + Σ_{i=1}^{start(j)} t_i - t_{start(j)}
    end while
    length(j) ← i - start(j)
    displacement(j) ← D · d
    d ← 0
    if i = n then
        p_occurrence(1..j) ←
            discretize(displacement(1..j),length(1..j))
        return p_occurrence(1..j),start(1..j)
    end if
    j ← j + 1
end while
```

Note that in contrast to the motif discovery technique, the improved technique leverages domain specific attributes of data (here, being the motion sensor data, which is used frequently in wearable sensors). Regardless of the technique used to discover recurrent activity patterns in single-dimensional time series, the output of this phase is passed to the multi-dimensional activity detection phase, which is described in the next section 3.3 Activity Structure in Multi-Dimensional Time Series In one embodiment, by using three-dimensional accelerometers, depending on motions included in an activity, the motions are projected on one, two, or three dimensions of the accelerometer. Since the original orientation and placement of the accelerometer is unknown, all dimensions can be considered together in order to discover recurrent activity. If a subset of dimensions is used for detecting the occurrence of activities, activities with similar projection may be classified together, and can be over-counted. In one embodiment, a graph clustering approach is used to derive an activity structure in multi-dimensional data. This stage groups several activity primitives from different dimensions together according to their temporal characteristics. In one embodiment, a general notion of temporal overlap is used to specify a set of primitives as an activity structure.

In order to derive multi-dimensional activity structures, a list of discovered activity primitives is converted into a weighted directed graph, so that graph clustering can be applied to derive a model of activities in multi-dimensional data. In the proposed graph, each vertex represents an activity primitive, and the weight on the vertex represents the number of occurrences of the primitive in the corresponding time series. The weight on each directed edge in the graph is calculated by the following equation:

$$e(i,\ j) = \frac{\text{coincidence}(i,\ j)}{\text{total\_occurences}(j)}$$

The coincidence(i, j) denotes the number of times that there is temporal overlap between occurrences of primitives i and j. As a result, e(i, j) will be at most 1, when all the occurrences of primitive j have overlap with occurrences of primitive i, and is at least 0, when there is no overlap between occurrences of primitives i and j.

Next, in one embodiment, a graph clustering approach is used to derive multi-dimensional activities structure from the primitive coincidence graph. Methodology 2, shown in Table 4, presents a technique for deriving the activity structures from the coincidence graph. Clustering the primitives starts with sorting the list of vertices based on the number of occurrences of the primitives. Then, the most frequent primitive is selected as a candidate core for the activity structure, and the graph is searched for primitives with high temporal correlation (e.g., temporal overlap) with the candidate core primitive. If there are several primitives with equal frequency, the one with the larger number of highly correlated neighbors is selected as the core primitive. The threshold for the correlation is set to $1-\beta$, where $\beta$ is an abnormality frequency constant. Upon construction of an activity by clustering correlated primitives, selected primitives are removed from the graph, and the methodology continues for discovering new activity structures by selecting a new core activity primitive.

TABLE 4

Methodology 2: Activity structure construction from the primitives coincidence graph 1: Input: G(V,E) the primitives coincidence graph,
    total_occurrence(v) for all vertices and $e(v_1,v_2)$ for all directed edges
2: Output: S = {$S_i$} The set of most recurrent activity structures in the time series, (each $S_i$ is an activity)
3: Sort the vertices list in G in descending order of total_occurrence
    {if some primitives have equal frequency, then the primitive with the highest number of highly correlated neighbors has the highest priority }

TABLE 4-continued

Methodology 2: Activity structure construction from the primitives coincidence graph

```
 4:    for each vertex v_k in the sorted list of vertices do
 5:        Add v_k to activity S_i
 6:        for all neighbors of v_k, if e_{(j,k)} > 1 − β do
 7:            Add v_j to activity S_i
 8:            remove v_j from the graph
 9:        end for
10:        i ← i + 1
11:        Update the sorted list of vertices
12:    end for
13:    return S = {S_1,...,S_{i−1}}
```

FIG. 2(c) illustrates the results of applying the methodology to the coincidence graph in FIG. 2(b) (the weights in the graph are omitted for ease of readability). As is denoted in FIG. 2, the activity structure extracted contains primitives E, D, G, O, and N (G is the activity core primitive, due to its frequent number of occurrences). In one embodiment and for some applications, β can have a value from about 0.2 to about 0.8, such as from about 0.3 to about 0.7, from about 0.4 to about 0.65, from about 0.55 to about 0.65, and such as about 0.6. Note that the effective derivation of activity structures can depend on the frequency of primitives, and in some applications the frequency and coincidences are significantly higher. For example and for some applications, β can be set to less than or equal to about 0.2 or less than or equal to about 0.1, such as 0<β≤0.2 or 0<β≤0.1. The depicted graph is formed from a set of short time series and is selected to be relatively short to better illustrate the logic behind the technique.

4. Location Discovery

Once a walking interval (or another activity interval) is detected via the unsupervised technique, walking subsequences is analyzed to discover the location of a sensor, such as an accelerometer, on the body. Several frequency and time domain features can be extracted from the walking subsequences. In one embodiment, frequency domain features can be analyzed to evaluate the impact of each step on the accelerometer. In each step, the energy of the impact between the foot and the floor is distributed across the body. The closer the sensor is to the foot (the origin of the strike in each step), the stronger is the energy sensed by the accelerometer. Alternatively, or in addition, time domain features can be evaluated to analyze the motion range of the sensor in at least a subset or all three directions. For example, a tri-axial accelerometer measures data in three spatial dimensions, and a location of the accelerometer on the body can be determined by exploiting the notion that some limbs (e.g., forearms) move more freely than other body parts (e.g., chest).

Figure 3:
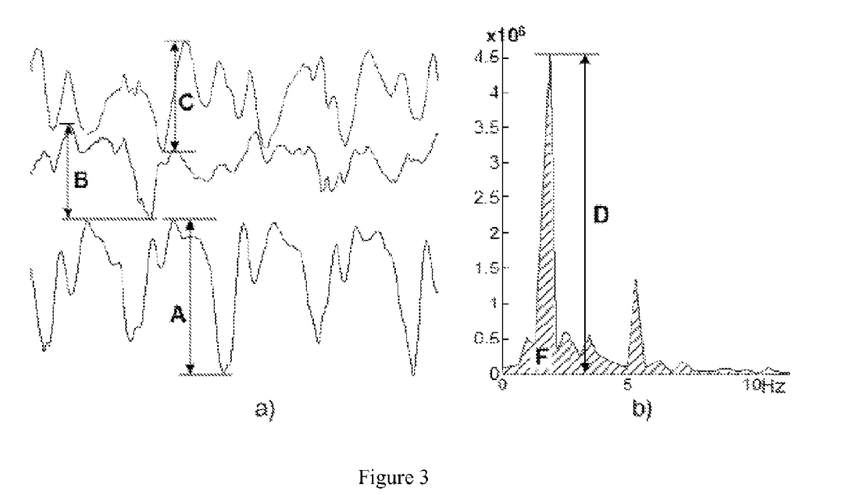
FIG. 3: (a) Accelerometer time series captured during walking in a sensor mounted on the forearm (3 second interval). (b) Power spectrum, according to an embodiment of the invention.

In addition to analyzing walking subsequences, the time series subsequences representing general activity (e.g., non-walking) also can be analyzed. In this regard, a technique is implemented to count the number of times the orientation of the device (body part) changes over time. In one embodiment, the technique first approximates the orientation of the sensor in each 10 second interval, via calculating the DC value of the Fourier transform. Alternatively, the time interval may be longer or shorter depending on the application. Then, the total number of orientation variations is calculated for a long time series by comparing the consecutive approximate orientations. Table 5 and FIG. 3 summarize six features extracted from walking and non-walking subsequences and the concept behind using them for location classification. FIG. 3(a) depicts a time series representing multiple walking steps in a 3 second interval (captured on the forearm). The power spectrum depicted in FIG. 3(b) is the sum of the frequency power spectrum of the three dimensions. As illustrated, feature A is the maximum amplitude among all the dimensions. A/C and A/B are the ratios of the maximum amplitudes in different axes. D and F represent the maximum energy (which is at 1.85 Hz in this embodiment) and the overall energy captured by the accelerometer, respectively. Note that although Table 5 presents 6 features, more or less features (e.g., 17 features) can be used in the SVM, which are variations of the presented features in the table.

TABLE 5

The Concept Behind the Six Major Extracted Features
(Letters in Parentheses Represent the Features in FIG. 3)

| Activity | Feature | Characteristic |
|---|---|---|
| Walking | Max energy in power spectrum (D) | Impact of strides on acceleration |
| Walking | Sum of energy in power spectrum (F) | |
| Walking | Maximuin of Max amplitudes for all axes (A > B, A > C) | Motion range |
| Walking | Ratio of amplitude in different axes $\left(\frac{A}{C}, \frac{A}{B}\right)$ | Degree of freedom in movement |
| Non-walk | Number of orientation variations | |

It is noteworthy that for each placement of the sensor on the body, the relation between coordinate systems of the sensor and the subject's body varies. Hence, no assumption is made during the feature extraction regarding the initial orientation of the sensor. As shown in Table 5, features either represent an accumulated value calculated among all the directions or depict the maximum of a property among the three dimensions.

Figure 4:
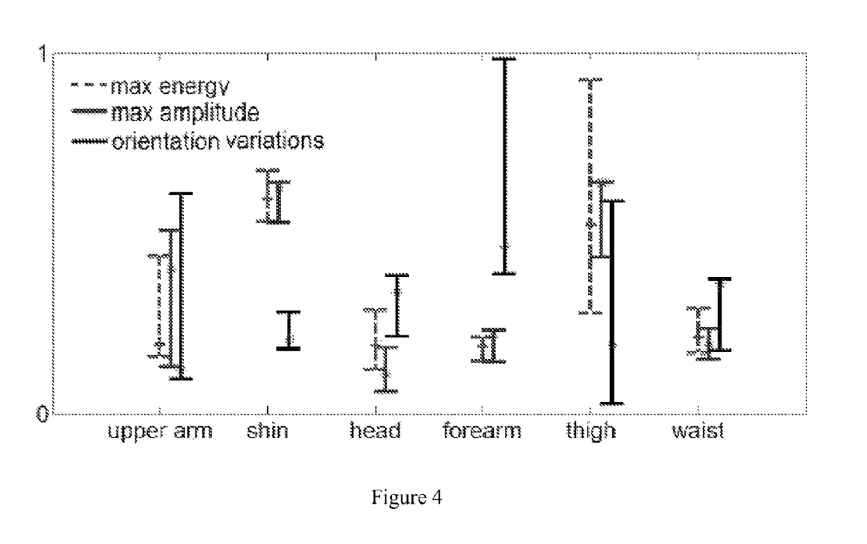
FIG. 4: Variation of three features for a subject in different sensor locations, according to an embodiment of the invention. Data is captured in a 5 minute time frame. Y axis is normalized. The leftmost feature for each sensor location (shown with dotted lines) is the maximum energy of the power spectrum, the center feature for each sensor location is the maximum amplitude across all directions, and the rightmost feature for each sensor location is the average number of orientation variations in a 5 minute time frame.
Figure 5:
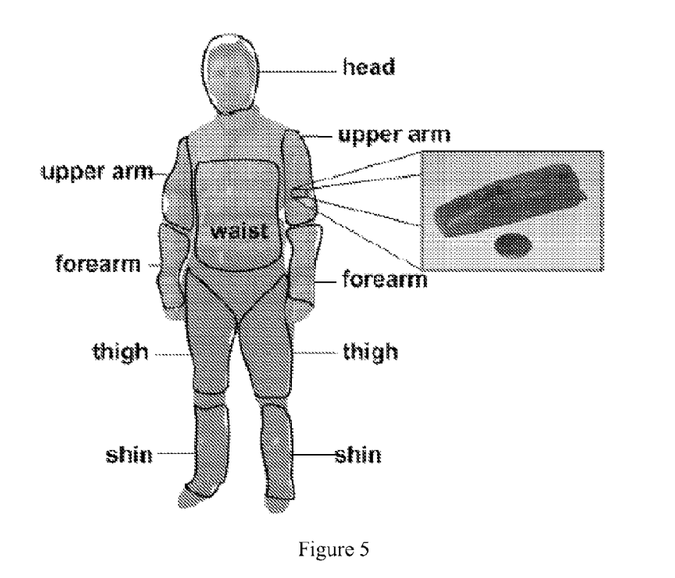
FIG. 5: Sensors are placed on 10 different regions of the body, according to an embodiment of the invention. The localization technique has 6 different outputs: {forearm, upper arm, head, thigh, shin, waist}.

FIG. 4 illustrates the variation of features A (maximum amplitude), D (maximum energy), and F (sum of the energy) for a subject, when the accelerometer is mounted on different parts on the body. As a result of stride variation, the features span over the normalized y axis. However, FIG. 4 shows that different locations exhibit different ranges for each feature. In the Example section, the performance of the SVM is evaluated in classifying the location of the sensors. In one embodiment, the sensors are classified into six different regions, as depicted in FIG. 5. Each of these regions has semi-independent movements during human activities. Alternatively, the sensors may be classified into more than six or fewer than six different regions, depending on the activity being monitored. For example, for some activities it is possible to distinguish the right forearm from the left forearm, which can increase the number of regions into which the sensors can be classified. Alternatively, or in addition, the regions shown in FIG. 5 can be further partitioned into smaller regions, which for some activities can be distinguished. In the Example section, experimental evaluation is presented for the classification technique for the six regions depicted in FIG. 5.

Once the location of a sensor is detected, some embodiments can generate an alert, a report, a log, or other indication of the sensor location, whether in visual form, audio form, tactile form, or a combination thereof. In some embodiments, identification of the sensor location can be used to calibrate sensor measurements or otherwise tune or adjust measurement data to account for a particular body part to which the sensor is applied. In some embodiments, identification of the sensor location can be used to automatically control operation or automatically select a particular operation mode of a device in which the sensor is included.

Figure 7:
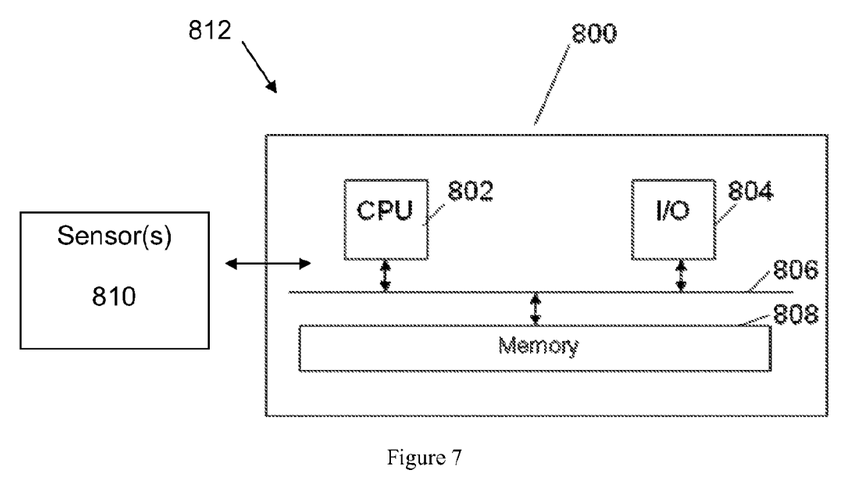
FIG. 7: A system configured in accordance with one embodiment of the invention.

FIG. 7 illustrates a system 812 configured in accordance with one embodiment of the present invention. The system 812 includes a computer 800, which includes a central processing unit (CPU) 802 connected to a bus 806. Input/output (I/O) devices 804 are also connected to the bus 806, and can include a keyboard, mouse, display, and the like. An executable program including a set of modules for discovering activities and sensor placement as described above is stored in memory 808, which is also connected to the bus 806. For example, the memory 808 can store an activity primitive extraction module to execute methodology 1, an activity structure derivation module to execute methodology 2, and a sensor placement identification module. The memory 808 can also store an alert module to generate alerts or other indications of sensor placement. The memory 808 can also store a control module to automatically control device operation or automatically select a particular device operation mode. As shown in FIG. 8, the system 812 also includes a set of sensors 810, which is connected to the computer 800 via a wired or wireless link, and from which time series data can be collected for processing by the computer 800. Although the sensors 810 are shown separate from the computer 800, these components can also be combined in other embodiments, such as within a monitoring device.

5. Example

Experimental Results

The following example describes specific aspects of an embodiment of the invention to illustrate and provide a description for those of ordinary skill in the art. The example should not be construed as limiting the invention, as the example merely provides specific methodology useful in understanding and practicing some embodiments of the invention.

An acceleration logging device from Gulf Coast Data Concepts is used to conduct experiments. The tri-axial accelerometer in the device has ±6 g gain and, therefore, its sensed acceleration does not saturate during normal activities. The sampling rate is set to 160 Hz. The device is suitable for long intervals of data collection because it has 1 GB of memory. In addition, the size of the device is relatively small (1 in×3.5 in×0.75 in) and does not interfere with normal activities of the subjects.

25 subjects (20 males, 5 females) participated in the study. Each subject wore 10 sensors on 10 different parts of his/her body, according to the sample setup shown in FIG. 5. No instruction was given to the users regarding the exact placement and the orientation of the sensors, and users were allowed to place the devices anywhere in the requested body parts. Subjects were allowed to choose to attach the sensors to the skin or to put them on their clothes. Each subject had sensors on for 30 minutes, during which he/she was asked to perform a sample set of his/her own daily activities. The subjects were requested to include a number of walking intervals in their activities. The collected time series data was divided into 3 minute subsequences. A total of 2500 time series samples were collected in this phase. A radial basis function (RBF) was used for the SVM kernel function. Cross-validation and grid-search techniques were used to find the optimal parameters for the kernel function.

5.1 Walking Interval Discovery

Figure 6:
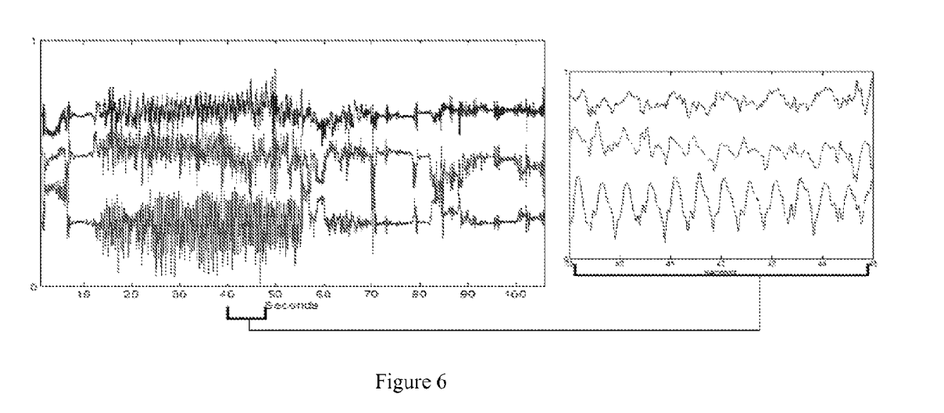
FIG. 6: Acceleration data collected from a sensor positioned on the arm during a 105 seconds interval (left), according to an embodiment of the invention. The magnified interval (right) depicts several occurrences of a walking activity. Y axis is normalized, and X, Y, and Z acceleration dimensions are shifted to enhance the presentation.

For each sample, the walking intervals were discovered via the unsupervised technique for recurrent activity detection. About 96% of the time series samples were detected to include walking intervals. This rate is high since the subjects were requested to include walking intervals in their activity. The walking discovery technique had a consistent accuracy in detecting walking occurrences in the time series. On average, about 93% of all walking strides were discovered and classified correctly. In discovering the walking occurrences, the highest accuracy was in the foot area with about 95% accuracy, and the lowest was in hand area (about 89%) due to the high variation in the motion patterns. FIG. 6 depicts an example of data collected from a sensor placed on a subject's arm. On average, about 2% false positive detection was observed, which denotes the number of non-walking activity occurrences that were labeled as walking Since the focus was to find relatively longer walking time intervals, the effect of false positives was effectively eliminated as these occurrences were sparsely distributed in the time series data.

5.2 Sensor Location Detection

In a first experiment, the localization SVM was trained and tested for each subject separately. Of the 100 time series samples collected from each subject, 20 samples were used for training, and the remaining 80 were used for testing. As expected, the classification result was near perfect, since the motion characteristics for each subject are consistent during his/her activity. The minimum, mean, and maximum overall classification precision for 25 subjects were about 88%, about 94%, and about 100%, respectively. However, having training data from each subject may not be a valid assumption in real life scenarios, where the technique is designed to work on off-the-shelf devices and for unknown users. Hence in a second experiment, the SVM was trained using 500 randomly selected samples out of 2500 time series. The average classification accuracy in this scenario was about 89%. Table 6 presents the classification precision and recall rate for each region separately.

TABLE 6

Classification Precision and Recall for Different Regions of the Body, When the Training and Testing Were Done Across Several Subjects

|  | upper arm | forearm | waist | shin | thigh | head |
|---|---|---|---|---|---|---|
| Precision | 83% | 93% | 100% | 88% | 92% | 84% |
| Recall | 91% | 100% | 63% | 85% | 87% | 94% |

Table 7 presents the details of false classifications for each region on the body. In this embodiment, the head has the lowest classification accuracy, because it generally mimics the motion characteristics of the upper extremities. Classification of the shin area is performed substantially perfectly, since the impact of each step on the shin area is significantly higher than other locations.

TABLE 7

Detailed Classification Results for Each Body Location

|  |  | Inferred location | | | | | |
| --- | --- | --- | --- | --- | --- | --- | --- |
|  |  | upper arm | forearm | waist | shin | thigh | head |
| Real location | upper arm | 88% | 6% | 3% | 3% | 0% | 0% |
|  | forearm | 11% | 85% | 0% | 0% | 4% | 0% |
|  | waist | 5% | 0% | 95% | 0% | 0% | 0% |
|  | shin | 0% | 0% | 0% | 100% | 0% | 0% |
|  | thigh | 0% | 0% | 0% | 12% | 88% | 0% |
|  | head | 18% | 10% | 9% | 0% | 0% | 63% |

An embodiment of the invention relates to a non-transitory computer-readable storage medium having computer code thereon for performing various computer-implemented operations. The term "computer-readable storage medium" is used herein to include any medium that is capable of storing or encoding a sequence of instructions or computer codes for performing the operations, methodologies, and techniques described herein. The media and computer code may be those specially designed and constructed for the purposes of the invention, or they may be of the kind well known and available to those having skill in the computer software arts. Examples of computer-readable storage media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits ("ASICs"), programmable logic devices ("PLDs"), and ROM and RAM devices. Examples of computer code include machine code, such as produced by a compiler, and files containing higher-level code that are executed by a computer using an interpreter or a compiler. For example, an embodiment of the invention may be implemented using Java, C++, or other object-oriented programming language and development tools. Additional examples of computer code include encrypted code and compressed code. Moreover, an embodiment of the invention may be downloaded as a computer program product, which may be transferred from a remote computer (e.g., a server computer) to a requesting computer (e.g., a client computer or a different server computer) via a transmission channel. Another embodiment of the invention may be implemented in hardwired circuitry in place of, or in combination with, machine-executable software instructions.

While the invention has been described with reference to the specific embodiments thereof, it should be understood by those skilled in the art that various changes may be made and equivalents may be substituted without departing from the true spirit and scope of the invention as defined by the appended claims. In addition, many modifications may be made to adapt a particular situation, material, composition of matter, method, operation or operations, to the objective, spirit and scope of the invention. All such modifications are intended to be within the scope of the claims appended hereto. In particular, while certain methods may have been described with reference to particular operations performed in a particular order, it will be understood that these operations may be combined, sub-divided, or re-ordered to form an equivalent method without departing from the teachings of the invention. Accordingly, unless specifically indicated herein, the order and grouping of the operations is not a limitation of the invention.

What is claimed is:

1. A non-transitory computer-readable storage medium, comprising executable instructions to:
   receive time series data including components in a plurality of dimensions, wherein the time series data correspond to measurements of a sensor that has been applied to a subject;
   determine a plurality of subsequences associated with the time series data, wherein each of the plurality of subsequences represents a characteristic pattern projected along one of the plurality of dimensions;
   identify a correlated subset of the plurality of subsequences as at least one instance of an activity of the subject; and
   based on features of the correlated subset, determine a location of where the sensor has been applied to the subject,
   wherein the executable instructions to determine the plurality of subsequences include executable instructions to:
      determine at least one subsequence as disposed between two consecutive stable regions in the time series data.

2. The non-transitory computer-readable storage medium of claim 1, wherein the executable instructions to identify the correlated subset include executable instructions to:
   perform graph clustering on vertices corresponding to the plurality of subsequences.

3. The non-transitory computer-readable storage medium of claim 2, wherein the executable instructions to perform the graph clustering include executable instructions to:
   assign weights to the vertices based on a degree of temporal overlap of respective pairs of the vertices.

4. The non-transitory computer-readable storage medium of claim 1, wherein the activity corresponds to walking, and the correlated subset corresponds to walking subsequences.

5. The non-transitory computer-readable storage medium of claim 1, wherein the executable instructions to determine the location of the sensor include executable instructions to:
   derive at least one feature based on a frequency domain representation of the correlated sub set.

6. The non-transitory computer-readable storage medium of claim 1, wherein the executable instructions to determine the location of the sensor include executable instructions to:
   derive at least one feature based on a time domain representation of the correlated subset.

7. The non-transitory computer-readable storage medium of claim 1, wherein the features of the correlated subset are indicative of at least one of a stride impact, a motion range, or a degree of freedom.

8. The non-transitory computer-readable storage medium of claim 1, wherein the executable instructions to determine the location of the sensor include executable instructions to:
   identify a body part of the subject to which the sensor is applied.

9. The non-transitory computer-readable storage medium of claim 1, further comprising executable instructions to:
   calibrate the measurements of the sensor based on the location of the sensor.

10. The non-transitory computer-readable storage medium of claim 1, further comprising executable instructions to:
    control operation of the sensor based on the location of the sensor.

11. A system for sensor localization, comprising:
a processing unit; and
a memory connected to the processing unit and including executable instructions to:
- identify a portion of a multi-dimensional time series as at least one instance of physical movement of a subject, wherein the multi-dimensional time series correspond to measurements of a sensor that has been applied to the subject;
- selectively process the portion of the multi-dimensional time series to derive a set of features associated with the physical movement; and
- based on the set features, determine a location of where the sensor has been applied to the subject, wherein the executable instructions to identify the portion of the multi-dimensional time series include executable instructions to:
- determine, within the portion of the multi-dimensional time series, at least one subsequence as disposed between two consecutive stable regions in the multi-dimensional time series.

12. The system of claim 11, wherein the executable instructions to identify the portion of the multi-dimensional time series include executable instructions to:
- identify, within the portion of the multi-dimensional time series, a set of subsequences that are correlated in time.

13. The system of claim 11, wherein the executable instructions to selectively process the portion of the multi-dimensional time series include executable instructions to derive at least one of:
- an accumulated value associated with the portion of the multi-dimensional time series; and
- a maximum value associated with the portion of the multi-dimensional time series.

14. The system of claim 11, wherein the executable instructions to determine the location of the sensor include executable instructions to:
- perform a supervised classification to assign a region of the subject as corresponding to the set of features.

15. The system of claim 11, wherein the sensor corresponds to an accelerometer, and the multi-dimensional time series correspond to acceleration data in a plurality of dimensions.

16. The system of claim 11, wherein the memory further includes executable instructions to:
- control operation of the sensor based on the location of the sensor.

17. The system of claim 11, wherein the memory further includes executable instructions to:
- calibrate the measurements of the sensor based on the location of the sensor.

* * * * *